(12) United States Patent
Kourtakis et al.

(10) Patent No.: US 7,700,812 B2
(45) Date of Patent: Apr. 20, 2010

(54) CATALYTIC CONVERSION OF ETHANOL TO A 1-BUTANOL-CONTAINING REACTION PRODUCT USING A THERMALLY DECOMPOSED HYDROTALCITE CONTAINING THE ANION OF ETHYLENEDIAMINETETRAACETIC ACID

(75) Inventors: Kostantinos Kourtakis, Media, PA (US); Michael B. D'Amore, Wilmington, DE (US); Leo Ernest Manzer, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 55 days.

(21) Appl. No.: 12/196,578

(22) Filed: Aug. 22, 2008

(65) Prior Publication Data

US 2009/0054672 A1 Feb. 26, 2009

Related U.S. Application Data

(60) Provisional application No. 60/965,727, filed on Aug. 22, 2007.

(51) Int. Cl.
*C07C 29/34* (2006.01)
*C07C 29/32* (2006.01)

(52) U.S. Cl. ............... 568/902.2; 568/902; 568/905

(58) Field of Classification Search ........... 568/902, 568/902.2, 905
See application file for complete search history.

(56) References Cited

U.S. PATENT DOCUMENTS 1,992,480 A 2/1935 Fuchs et al.
5,300,695 A 4/1994 Radlowski

FOREIGN PATENT DOCUMENTS

WO 2006059729 A1 6/2006

OTHER PUBLICATIONS

International Search Report and Written Opinion, International Application No. PCT/US2008/073943, filed Aug. 22, 2008.
W. Ueda et al., "Condensation of alcohol over solid-base catalyst to form higher alcohols", Catalysis Letters, vol. 12, 1992, pp. 97-104. XP002497783 p. 99; table 1.
F. Cavani et al., "Hydrotalcite-type anionic clays: preparation, properties and applications", Catalysis Today, vol. 11, Jan. 1, 1991, pp. 173-301, XP002497610 pp. 186-189.
J. Logsdon, Kirk-Othmer Encyclopedia of Chemical Technology, 2001, John Wiley & Sons (Book Not Included—Available Upon Request).
M. N. Dvornikoff et al., Condensation of Alcohols, J. of Organic Chemistry, 1957, vol. 11:540-542.
J. I. Dicosimo et al., Structural Requirements and Reaction Pathway in Condensation Reactions of Alcohols on MG AIO Catalysts, Journal of Catalysis, 2000, vol. 190:261-275.
J. I. Dicosimo et al., Structure and Surface and Catalytic Properties of MG-A1 Basic Oxides, Journal of Catalysis, 1998, vol. 178:499-510.
C. Carlini et al., Guerbet Condensation of Methanol With N-Propanol to Isobutyl Alcohol Over Heterogeneous Bifunctional Catalysts Based on MG-A1 Mixed Oxides Partially Sunstituted by Different Metal Components, Journal of Molecular Catalysis A: Chemical, 2005, vol. 232:13-20.
C. Carlini et al., Guerbet Condensation of Methanol With N-Propanol to Isobutyl Alcohol Over Heterogeneous Copper Chromite/MG-A1 Mixed Oxides Catalysts, Journal of Molecular Catalysis A: Chemical, 2004, vol. 220:215-220.
V. K. Diez et al., Effect of the Acid-Base Properties of MG-A1 Mixed Oxides on the Catalyst Deactivation During Aldol Condensation Reactions, Latin American Applied Research, 2003, vol. 33:79-86.
N. N. Das et al., Catalytic Characterization of Bi-Functional of Bi-Functional Catalysts Derived From PD-MG-A1 Layered Double Hydroxides, Bull. Mater. Sci., 2002, vol. 25:283-289.
H. S. Fogler, Elements of Chemical Reaction Enginerring, 2nd Edition,, 1992, (Book Not Included—Available Upon Request).

*Primary Examiner*—Elvis O Price

(57) ABSTRACT

Hydrotalcites containing the anion of ethylenediaminetetraacetic acid are partially or fully thermally decomposed to provide catalysts useful for the conversion of ethanol to a reaction product comprising 1-butanol.

12 Claims, 2 Drawing Sheets

US 7,700,812 B2

CATALYTIC CONVERSION OF ETHANOL TO A 1-BUTANOL-CONTAINING REACTION PRODUCT USING A THERMALLY DECOMPOSED HYDROTALCITE CONTAINING THE ANION OF ETHYLENEDIAMINETETRAACETIC ACID

CROSS-REFERENCE TO RELATED APPLICATIONS

This application claims benefit of priority from Provisional Application No. 60/965727, filed Aug. 22, 2007. This application relates to commonly-assigned applications filed concurrently on Aug. 22, 2008 as Ser. Nos. 12/196,485, 12/196,518, 12/196,540, 12/196,602, and 12/196,651.

FIELD OF THE INVENTION

The present invention relates to the catalytic conversion of ethanol to a 1-butanol-containing reaction product. Various organic chemicals, including 1-butanol itself, can be separated from the reaction product. The catalysts are hydrotalcites, optionally containing transition metals, that contain the anion of ethylenediaminetetraacetic acid, that have been thermally decomposed, either partially or fully, to form catalytically active species.

BACKGROUND

Efforts directed at improving air quality and increasing energy production from renewable resources have resulted in renewed interest in alternative fuels, such as ethanol and butanol, that might replace gasoline and diesel fuel, or be used as additives in gasoline and diesel fuel.

It is known that 1-butanol can be prepared by condensation from ethanol over basic catalysts at high temperature using the so-called "Guerbet Reaction." See for example, J. Logsdon in Kirk-Othmer Encyclopedia of Chemical Technology, John Wiley and Sons, Inc., New York, 2001.

Methods of using catalysts to convert ethanol to butanol are also discussed in the following references.

M. N. Dvornikoff and M. W. Farrar, J. of Organic Chemistry (1957), 11, 540-542, disclose the use of MgO—$K_2CO_3$—$CuCrO_2$ catalyst system to promote ethanol condensation to higher alcohols, including 1-butanol. The disclosed liquid phase reaction using this catalyst showed a 13% conversion of ethanol and 47% selectivity to 1-butanol.

U.S. Pat. No. 5,300,695, assigned to Amoco Corp., discloses processes in which an alcohol having X carbon atoms is reacted over an L-type zeolite catalyst to produce a higher molecular weight alcohol. In some embodiments, a first alcohol having X carbon atoms is condensed with a second alcohol having Y carbon atoms to produce an alcohol having X+Y carbons. In one specific embodiment, ethanol is used to produce butanol using a potassium L-type zeolite.

J. I. DiCosimo, et al., in Journal of Catalysis (2000), 190 (2), 261-275, describe the effect of composition and surface properties on alcohol-coupling reactions using $Mg_yAlO_x$ catalysts for alcohol reactions, including ethanol. Also condensation reactions on $Mg_yAlO_x$ samples involved the formation of products containing a new C—C bond, such as n-$C_4H_8O$ (or n-$C_4H_9OH$) and iso-$C_4H_8O$ (or iso-$C_4H_9OH$). They also describe, in Journal of Catalysis (1998), 178(2), 499-510, that the oxidation to acetaldehyde and the aldol condensation to n-butanol both involve initial surface ethoxide formation on a Lewis acid-strong base pair.

WO 2006059729 (assigned to Kabushiki Kaisha Sangi) describes a process for efficiently producing, from ethanol as a raw material, higher molecular weight alcohols having an even number of carbon atoms, such as 1-butanol, hexanol and the like. The higher molecular weight alcohols are yielded from ethanol as a starting material with the aid of a calcium phosphate compound, e.g., hydroxyapatite $Ca_{10}(PO_4)_6(OH)_2$, tricalcium phosphate $Ca_3(PO_4)_2$, calcium monohydrogen phosphate $CaHPO_4 \times (0\text{-}2)H_2O$, calcium diphosphate $Ca_2P_2O_7$, octacalcium phosphate $Ca_8H_2(PO_4)_6 \times 5H_2O$, tetracalcium phosphate $Ca_4(PO_4)_2O$, or amorphous calcium phosphate $Ca_3(PO_4)_2 \times nH_2O$, preferably hydroxyapatite, as a catalyst, the contact time being 0.4 second or longer.

Carlini et al. describe a catalytic reaction of methanol with n-propanol to produce isobutyl alcohol. The involved catalyst is a calcined hydrotalcite in combination with copper chromite. See C. Carlini et al, Journal of Molecular Catalysis A: Chemical (2005), 232 (1-2) 13-20. See also C. Carlini, Journal of Molecular Catalysis A: Chemical (2004), 220 (2), 215-220, in which the catalyst is a mixture of a hydrotalcite with Pd, Ni, Rh, or Cu, with the mixture being calcined at 500° C.

Hydrotalcites are layered, double hydroxides of the general formula

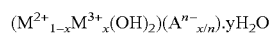

$$(M^{2+}_{1-x}M^{3+}_x(OH)_2)(A^{n-}_{x/n}) \cdot yH_2O$$

The $M^{2+}$ ions can be a variety of divalent cations (e.g., Mg, Ni, Pt, Pd, Zn, Co, Fe, Cu) and the $M^{3+}$ ions can be trivalent Al, Fe or Cr. Some hydrotalcites are described by V. K. Diez, C. R. Apesteguia, and J. I. DiCosimo (Latin American Applied Research, 33, 79-86 (2003)) and N. N. Das and S. C. Srivastava (Bull. Mater. Sci. 25, (4), 283-289 (2002)).

It has been found that partially or fully thermally decomposed hydrotalcites that incorporate the anion of ethylenediaminetetraacetic acid, can yield catalysts that are effective for the conversion of ethanol to a reaction product that comprises (i.e., contains among other things) 1-butanol.

SUMMARY OF THE INVENTION

Certain hydrotalcites, as described herein, are partially or fully thermally decomposed to provide catalysts useful for the conversion of ethanol to a 1-butanol-containing reaction product.

DESCRIPTION

Figure 1:
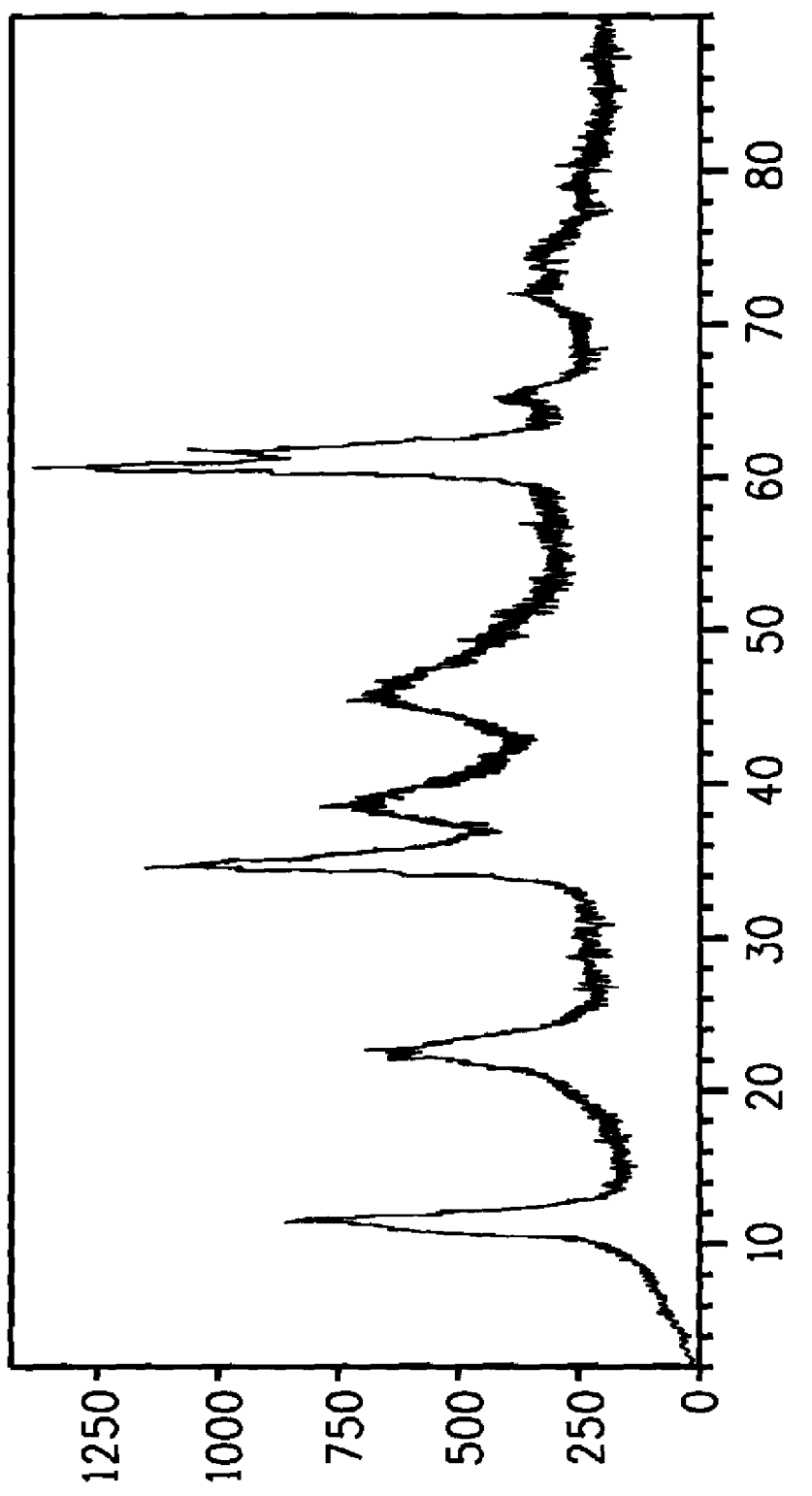
FIG. 1 shows the powder X-ray diffraction pattern of the hydrotalcite material of Example 1 before calcination, and indicates reflections typical of a hydrotalcite phase.
Figure 2:
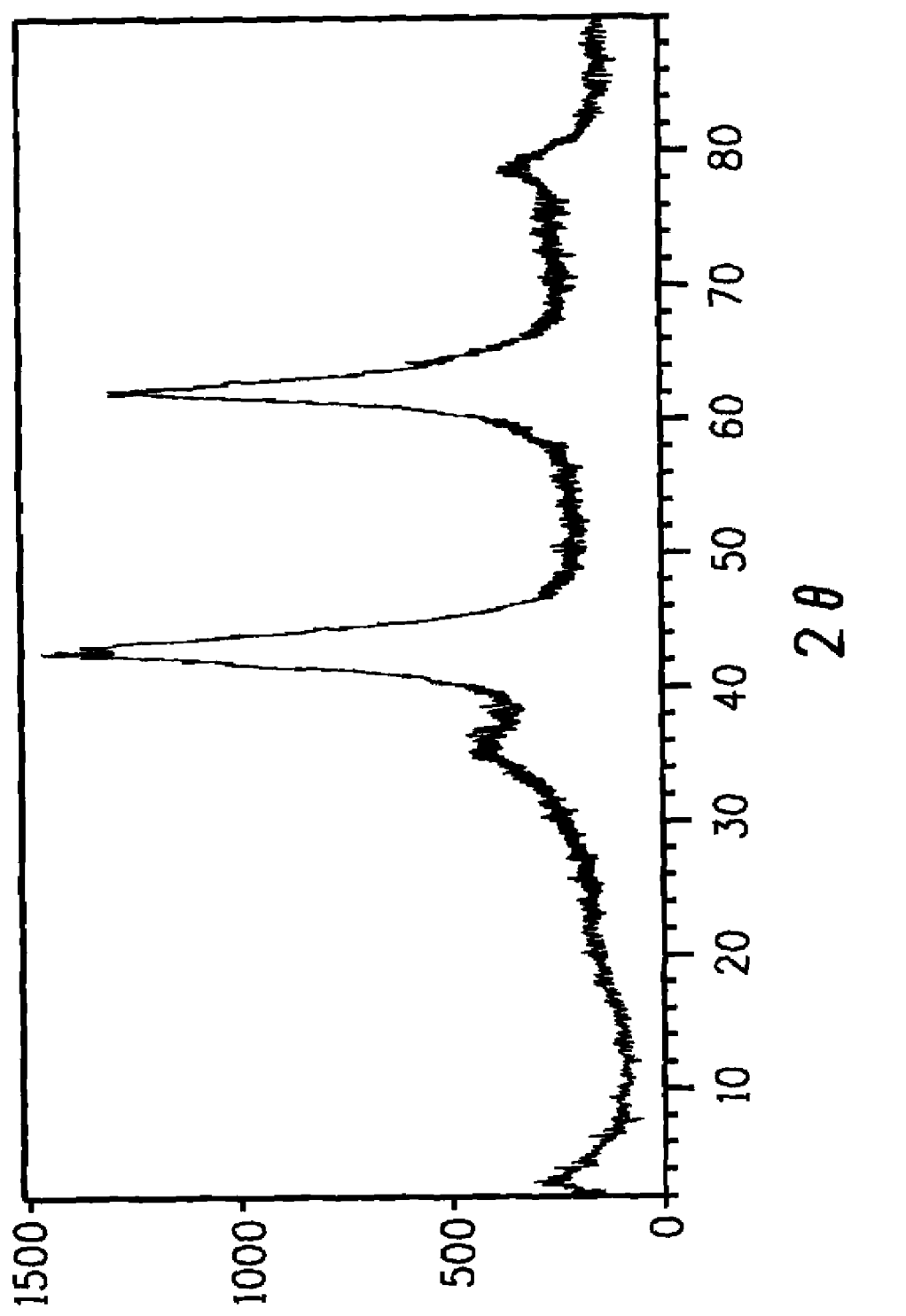
FIG. 2 shows a powder X-ray diffraction pattern of the material of FIG. 1 after calcination, showing decomposition of the hydrotalcite phase by the substantial loss of those reflections that are typical of a hydrotalcite phase.

A stream of gas phase ethanol (that may contain water, and may be diluted with an inert gas such as nitrogen and carbon dioxide) is contacted with at least one thermally decomposed hydrotalcite catalyst at a temperature and pressure sufficient to produce a reaction product comprising water unreacted ethanol (if less than complete ethanol conversion), butanol, higher alcohols and other organic species. The butanol is predominantly 1-butanol. Suitable temperatures are in the range of about 150° C. to about 500° C., for example about 200° C., to about 500° C. Suitable pressures are from about 0.1 MPa to about 20.7 MPa.

The catalysts that are useful in the present invention are partially or fully thermally decomposed hydrotalcites of the empirical formula

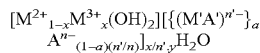

$$[M^{2+}{}_{1-x}M^{3+}{}_x(OH)_2][\{(M'A')^{n'-}\}_a A^{n-}{}_{(1-a)(n'/n)}]_{x/n'\cdot y}H_2O$$

wherein $M^{2+}$ is divalent Mg, or a combination of divalent Mg and at least one divalent member selected from the group consisting of Zn, Ni, Pd, Pt, Co, Fe, and Cu;

$M^{3+}$ is trivalent Al, or a combination of trivalent Al and at least one trivalent member selected from the group consisting of Fe and Cr;

x is 0.66 to 0.1;

M' is (i) one or more divalent members selected from the group consisting of Zn, Ni, Pd, Pt, Fe, Co, and Cu; or (ii) one or more trivalent members selected from the group consisting of Fe, Cr, and Ru; or (iii) a mixture of one or more of said divalent members with one or more of said trivalent members;

A' is the anion of ethylenediaminetetraacetic acid;

n' is the absolute value of the sum of the oxidation state of M' (i.e., +2 if M' is one or more divalent members or +3 if M' is one or more trivalent members) and the oxidation state of the anion of ethylenediaminetetraacetic acid (−4) (for example, for M'A' wherein M' is $Zn^{2+}$ with an oxidation state of +2, n' is +2); provided that if M' is said mixture, then n' is calculated according to the following equation:

$$n' = \text{the absolute value of } [X_D(2)+X_D(-4)+X_T(3)+X_T(-4)], \text{ wherein}$$

$X_D$ = the sum of the number of moles of all divalent members divided by (the sum of the number of moles of all divalent members+the sum of the number of moles of all trivalent members), and $X_T$ = the sum of the number of moles of all trivalent members divided by (the sum of the number of moles of all divalent members+the sum of the number of moles of all trivalent members);

$A^{n-}$ is $CO_3^{2-}$ with n=2 or $OH^-$ with n=1;

a=0.001 to 1; and y=0 to 4.

In a preferred embodiment, $M^{2+}$ is divalent Mg; $M^{3+}$ is trivalent Al; M' is Co, Cr, Cu or Ni; a=0.01 to 0.44; $A^{n-}$ is $CO_3^{2-}$ or $OH^-$.

Without wishing to be bound by theory, it is believed that the hydrotalcites of the formula above have the species M'A' intercalated into a hydrotalcite structure.

The catalysts that are useful in the present invention are derived from a hydrotalcite of the formula as defined above by a process comprising heating the hydrotalcite for a time and at a temperature sufficient to cause a diminution in the hydrotalcite powder X-ray diffraction pattern peak intensities between 2θ angles of 10 degrees and 70 degrees using CuKα radiation.

Catalysts derived from the hydrotalcite can be synthesized by the following preferred method. A first aqueous solution containing M'A' is prepared. The solution can be prepared by adding ethylenediaminetetraacetic acid (EDTA) to water, adding hydroxide (preferably NaOH) until the EDTA is dissolved in the water, followed by adding an M' salt, preferably a nitrate, chloride or acetate salt. Most preferred are nitrate salts. Sodium, potassium or ammonium hydroxide is then added until a pH of about 10 is reached. The solution is then warmed to a temperature of about 60° C. to 70° C., preferably 65° C. Next, a second aqueous solution of $M^{2+}$ and $M^{3+}$ salts is prepared by dissolving the salts in water. The second solution containing the $M^{2+}$ and $M^{3+}$ salts is added drop-wise to the first solution. Alternatively, a plurality of individual metal salt solutions may be used, provided that they are added concurrently to the solution containing EDTA and the M' salt. The resulting suspension is warmed to a temperature of about 60° C. to 70° C., preferably 65° C. During the addition of the second solution to the first solution, the pH of the resulting suspension is monitored and adjusted, if necessary, to maintain a pH of about 10 using hydroxide (with soluble metal carbonate or bicarbonate if $A^{n-}$ is chosen to be $CO_3^{2-}$.

The resulting suspension (i.e., a precipitate suspended in a liquid) can be aged, preferably for approximately 18 hours, at 60° C. to 70° C. The precipitate is then separated, generally by filtering, and subsequently dried (generally in a vacuum oven or in air). The dried precipitate can be analyzed by powder X-ray diffraction to confirm the presence of a hydrotalcite phase. This phase is isostructural with the hydrotalcite $Mg_6Al_2(CO_3)(OH)_{16} \cdot 4H_2O$ (JCPDS card # 54-1030; Powder Diffraction Files, International Centre for Diffraction Data, 1601 Park Lane, Swarthmore, Pa. 19081). The dried precipitate is then calcined, to achieve partial decomposition, by heating it for a time and at a temperature sufficient to cause a diminution in the hydrotalcite powder X-ray diffraction pattern peak intensities between 2θ angles of 10 degrees and 70 degrees using CuKα radiation. The calcined material can be analyzed by powder X-ray diffraction to confirm the diminution (including the complete absence) in these peak intensities and the appearance of new peaks corresponding to a material which is isostructural with partially crystalline magnesium oxide (MgO, JCPDS card # 65-0476). Partial decomposition is preferably achieved by calcining the dried precipitate for a time and at a temperature sufficient to substantially reduce the peak intensities characteristic of the hydrotalcite phase.

Although any calcination protocol can be used, one that is particularly useful on a laboratory scale includes heating the hydrotalcite in a one inch (2.5 cm) diameter tube furnace from about 25° C. to about 360° C. over 140 minutes at 2.4° C. per minute, and then holding at 360° C. for about 2 to about 4 hours.

The catalysts usable in the process of the invention can be prepared as described above. The catalysts may be used in the form of powders, granules, or other particulate forms. Selection of an optimal average particle size for the catalyst will depend upon such process parameters as reactor residence time and desired reactor flow rates.

The catalytic conversion of ethanol to the reaction product comprising 1-butanol can be run in either batch or continuous mode as described, for example, in H. Scott Fogler, (*Elements of Chemical Reaction Engineering*, 2nd Edition, (1992) Prentice-Hall Inc, CA). Suitable reactors include fixed-bed, adiabatic, fluid-bed, transport bed, and moving bed.

It is preferable, but not essential, to treat the catalyst, prior to its use, with nitrogen or air at elevated temperatures, which is thought to remove unwanted carbonates from the catalyst surface. If the starting hydrotalcite contains Ni, Pd, Pt, Co or Cu, it is also preferred, but not essential, to treat the catalyst, prior to its use, with hydrogen at elevated temperatures. One protocol that has been found to be effective is described in more detail in the Examples, below. If catalyst treatment is desired, the catalyst may be treated in situ in the reactor or ex situ and then introduced into the reactor.

During the course of the reaction, the catalyst may become fouled, and therefore it may be necessary to regenerate the catalyst. Preferred methods of catalyst regeneration include, contacting the catalyst with a gas such as, but not limited to, air, steam, hydrogen, nitrogen or combinations thereof, at an elevated temperature, although care must be taken not to use a temperature that is so high that the regeneration results in a loss of surface area or other unwanted effects. If catalyst regeneration is desired, the catalyst may be regenerated in situ in the reactor or ex situ and then introduced into the reactor.

One skilled in the art will know that conditions, such as temperature, catalytic metal, catalyst support, reactor configuration and time can affect the reaction kinetics, product yield and product selectivity. Standard experimentation can be used to optimize the yield of 1-butanol from the reaction.

1-Butanol can be separated from the reaction product by known chemical engineering methods, including distillation. Other specific chemicals (or combinations of chemicals) also can be removed from the reaction product using known chemical engineering methods. The specific methods will be dependent on the nature of the reaction product, which, in turn, is dependent on the specific catalyst used and the reaction conditions, particularly the extent of ethanol conversion.

Although particular embodiments of the present invention have been described in the foregoing description, it will be understood by those skilled in the art that the invention is capable of numerous modifications, substitutions, and rearrangements without departing from the spirit or essential attributes of the invention.

EXAMPLES

Example 1

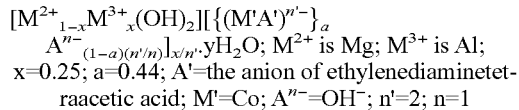

$x=0.25$; $a=0.44$; A'=the anion of ethylenediaminetetraacetic acid; M'=Co; $A^{n-}$=OH$^-$; n'=2; n=1

11.09 g of ethylenediaminetetraacetic acid (Sigma-Aldrich) was dissolved in 250 milliliters (ml) of water in a three neck, round bottom flask and heated to 65° C. Enough sodium hydroxide (2 M NaOH solution (J T Baker)) was added to completely dissolve the EDTA. 4.8 g of cobalt nitrate Co(NO$_3$)$_2$.6H$_2$O (Alfa) was then dissolved in the preheated solution containing EDTA. Following the addition of cobalt nitrate, the pH was adjusted to about 10 by adding 2 M NaOH solution (J T Baker). Separate solutions of aluminum nitrate and magnesium nitrate were prepared as follows: 27.5 g of aluminum nitrate (Al(NO$_3$)$_3$.9H$_2$O (EMD Sciences, Gibbstown, N.J., AX0705-11)), and 57.6 g of magnesium nitrate (Mg(NO$_3$)$_2$.6H$_2$O (EMD Sciences, MX0060-1)) were each dissolved in 100 ml of water, and the two solutions were added drop-wise (concurrently) to the preheated solution containing EDTA and cobalt. The time for this addition was about 45 minutes. During this addition, sodium hydroxide solution was added to maintain a pH of about 10. The preheated solution was stirred during the addition of the metal nitrates. After complete addition of these metal nitrates, the resulting suspension was kept at 65° C. with stirring for 1 hour (hr) and then aged at this temperature for 18 hours without stirring. The precipitate was separated from solution by filtering. The synthesized separated solids were dried in vacuum oven at 90° C. for 48 hrs and calcined at 360° C. for 2 hours in nitrogen. The heating protocol was as follows: the precipitate was placed in a 1 inch (2.5 cm) diameter tube furnace, and the temperature was increased from 25 to 360° C. at 2.4° C. per minute over the course of 140 minutes, followed by 360° C. for 2 hours. The catalyst was evaluated according to the following procedure.

Reactor Evaluation

Approximately 2 cubic centimeters (cc) of catalyst was loaded on a stainless steel mesh support within a 18 inch×½ inch (45.7 cm×1.3 cm) outside diameter (o.d.) type 360 stainless steel tube reactor with inlets for gas and liquid feeds. The catalyst was the pre-conditioned in situ in the reactor by flowing nitrogen gas, initially at room temperature, raising the temperature to 350° C., holding it there for one hour, lowering the temperature to 180° C., flowing hydrogen gas at 15 cc/min for one hour, reintroducing nitrogen gas at a flow rate of 15 cc/min, and increasing the reactor temperature to 300° C. to introduce the ethanol to generate reaction data. At reaction temperature nitrogen flow was set at 15 cc/min and ethanol flow at 1.03 ml/hr. After 60 minutes, reaction off-gases were condensed over a five minute period into cold N-methylpyrrolidone, and the resultant solution was analyzed using an Agilent™ 5890 GC equipped with flame ionization and mass selective detectors. Results are shown in Table 1, wherein "EtOH" means ethanol, "BuOH" means 1-butanol, "Conv." means conversion, and "Sel." means selectivity. Ethanol conversion (%) was calculated as follows: [(1−carbon moles of unreacted ethanol)/carbon moles of total outlet gases] times 100. Selectivity (%) was calculated as follows: (carbon moles of product/carbon moles of ethanol reacted) times 100.

TABLE 1

| Temp. ° C. | Minutes | EtOH Conv. | BuOH Sel. | Yield |
|---|---|---|---|---|
| 300 | 60 | 13.0 | 62.7 | 8.2 |
| 350 | 60 | 23.3 | 41.6 | 9.7 |
| 400 | 60 | 47.0 | 25.8 | 12.1 |

Example 2

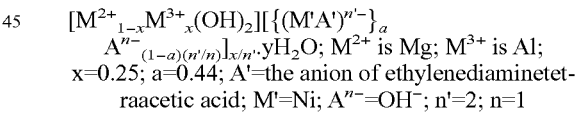

$x=0.25$; $a=0.44$; A'=the anion of ethylenediaminetetraacetic acid; M'=Ni; $A^{n-}$=OH$^-$; n'=2; n=1

11.09 g of ethylenediaminetetraacetic acid (Sigma-Aldrich) was dissolved in 250 ml of water in a three neck, round bottom flask and heated to 65° C. Enough sodium hydroxide (2 M NaOH solution (J T Baker)) was added to completely dissolve the EDTA. 4.8 g of nickel nitrate (Ni(NO$_3$)$_2$.6 H$_2$O (Aldrich)) was then dissolved in the preheated solution containing the EDTA. Following the addition of nickel nitrate, the pH was adjusted to about 10 by adding 2 M NaOH solution (J T Baker). Separate solutions of aluminum nitrate and magnesium nitrate were prepared as follows: 27.5 g of aluminum nitrate (Al(NO$_3$)$_3$.9H$_2$O (EMD Sciences, AX0705-11)) was dissolved in 100 ml of water, and 57.6 g of magnesium nitrate (Mg(NO$_3$)$_2$.6H$_2$O (EMD Sciences, MX0060-1)) was dissolved in 100 ml of water. The two solutions were added drop-wise and concurrently to the preheated solution containing EDTA and nickel. The time for this addition was about 45 minutes. During this addition, sodium hydroxide solution was added to maintain a pH of about 10. The preheated solution was stirred during the addition of the metal nitrates. After complete addition of these metal nitrates, the suspension was kept at 65° C. with stirring for 1 hr and then aged at this temperature for 18 hours without stirring. The precipitate was separated from solution by filtering. The synthesized separated solids were dried in vacuum oven at 90° C. for 48 hrs and calcined at 360° C. for 2 hours in nitrogen. The heating protocol was as follows: the precipitate was placed in a 1 inch (2.5 cm) diameter tube furnace, and the temperature was increased from 25 to 360° C. at 2.4° C. per minute over the course of 140 minutes, followed by 360° C. for 2 hours. The catalyst was evaluated according to the procedure described in Example 1. Results are shown in Table 2.

TABLE 2

| Temp. ° C. | Minutes | EtOH Conv. | BuOH Sel. | Yield |
|---|---|---|---|---|
| 300 | 60 | 23.1 | 54.8 | 12.6 |
| 350 | 60 | 36.3 | 38.5 | 14.0 |
| 400 | 60 | 65.7 | 19.0 | 12.5 |

What is claimed is:

1. A process for making a 1-butanol-containing product, comprising:
   contacting a reactant comprising ethanol with a catalyst at a reaction temperature and pressure sufficient to produce said reaction product, wherein said catalyst is derived from a hydrotalcite of the formula:

$$[M^{2+}_{1-x}M^{3+}_x(OH)_2][\{(M'A')^{n'-}\}_a A^{n-}_{(1-a)(n'/n)}]_{x/n'} \cdot yH_2O$$

wherein
   $M^{2+}$ is divalent Mg, or a combination of divalent Mg and at least one divalent member selected from the group consisting of Zn, Ni, Pd, Pt, Co, Fe, and Cu;
   $M^{3+}$ is trivalent Al, or a combination of trivalent Al and at least one trivalent member selected from the group consisting of Fe and Cr;
   x is 0.66 to 0.1;
   M' is (i) one or more divalent members selected from the group consisting of Zn, Ni, Pd, Pt, Fe, Co, and Cu; or (ii) one or more trivalent members selected from the group consisting of Fe, Cr, and Ru; or (iii) a mixture of one or more of said divalent members with one or more of said trivalent members;
   A' is an anion of ethylenediaminetetraacetic acid;
   n' is an absolute value of a sum of an oxidation state of M' and (−4);
   provided that if M' is said mixture, then n' is calculated according to an equation:

$n'$=the absolute value of $[X_D(2)+X_D(-4)+X_T(3)+X_T(-4)]$, wherein $X_D$=sum of a number of moles of all divalent members divided by (sum of a number of moles of all divalent members+sum of a number of moles of all trivalent members), and
   $X_T$=sum of a number of moles of all trivalent members divided by (the sum of the number of moles of all divalent members+the sum of the number of moles of all trivalent members);
   $A^{n-}$ is $CO_3^{2-}$ with n=2 or $OH^-$ with n=1;
   a=0.001 to 1; and
   y=0 to 4;
   wherein the hydrotalcite catalyst is partially decomposed.

2. The process of claim 1, wherein the decomposition is achieved by heating for a time and at a temperature sufficient to cause a diminution in the hydrotalcite powder X-ray diffraction pattern peak intensities between 2θ angles of 10 degrees and 70 degrees using CuKα radiation.

3. The process of claim 1, wherein $M^{2+}$ is divalent Mg.

4. The process of claim 1, wherein $M^{+3}$ is Al.

5. The process of claim 1, wherein M' is Ni.

6. The process of claim 1, wherein M' Co.

7. The process of claim 1, wherein $A^{n-}$ is $OH^-$.

8. The process of claim 1, wherein n' is 2.

9. The process of claim 1, wherein n is 1.

10. The process of claim 1, wherein $M^{2+}$ is Mg; $M^{3+}$ is Al; x is 0.25; a is 0.44; A' is the anion of ethylenediaminetetraacetic acid; M' is Co; $A^{n-}$ is $OH^-$; n' is 2; n is 1.

11. The process of claim 1, wherein $M^{2+}$ is Mg; $M^{3+}$ is Al; x is 0.25; a is 0.44; A' is the anion of ethylenediaminetetraacetic acid; M' is Ni; $A^{n-}$ is $OH^-$; n' is 2; n is 1.

12. The process of claim 1, wherein said reaction temperature is from about 200° C. to about 500° C., and said pressure is from about 0.1 MPa to about 20.7 MPa.

* * * * *